Figure 1:
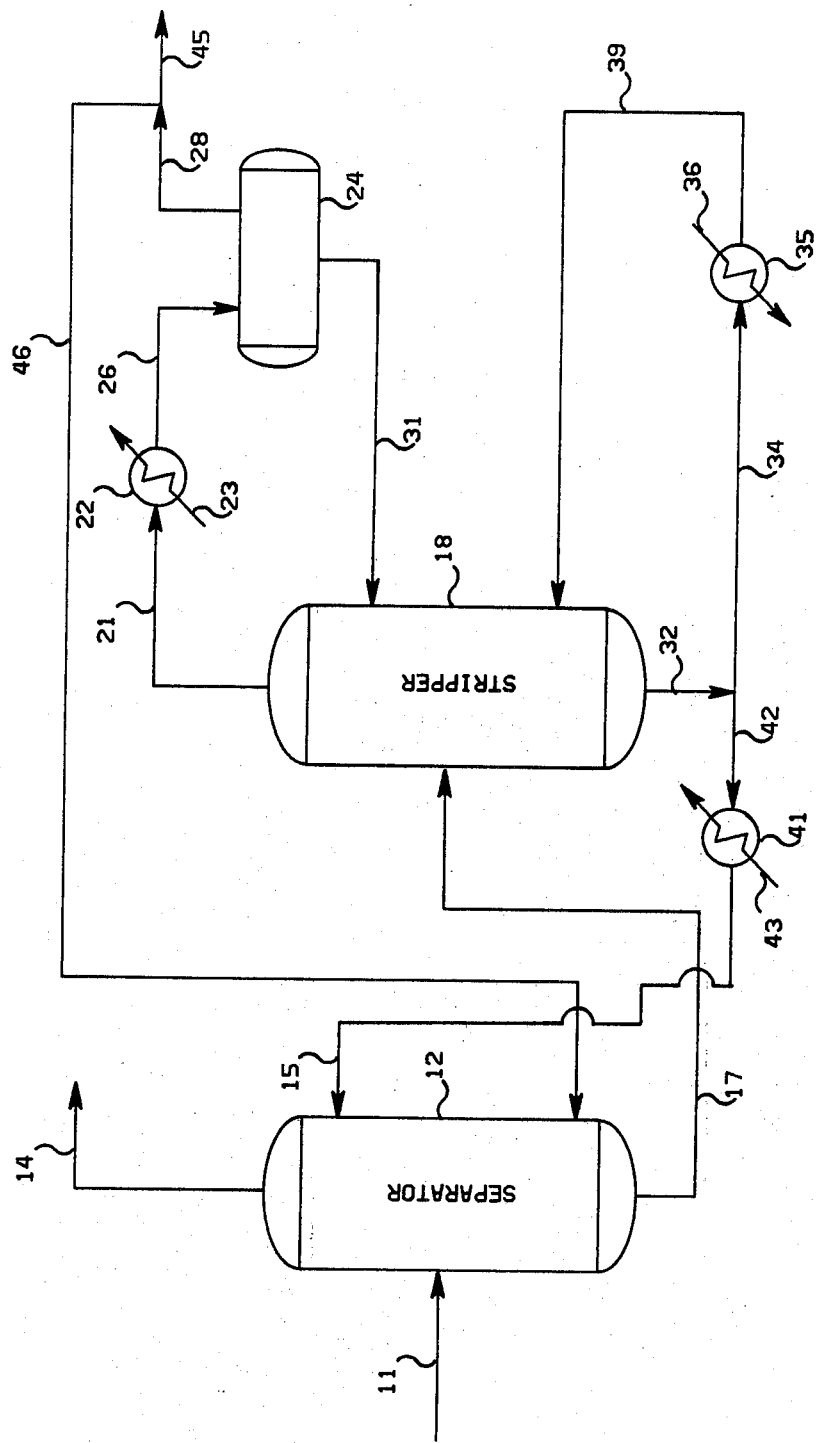

United States Patent [19]

Tabler et al.

[11] 4,398,052

[45] Aug. 9, 1983

[54] SEPARATION OF MONOOLEFINS FROM OTHER MONOOLEFINS

[75] Inventors: Donald C. Tabler; Marvin M. Johnson, both of Bartlesville, Okla.

[73] Assignee: Phillips Petroleum Company, Bartlesville, Okla.

[21] Appl. No.: 140,282

[22] Filed: Apr. 14, 1980

[51] Int. Cl.³ .......................................... C07C 7/148
[52] U.S. Cl. ................... 585/845; 260/438.1; 585/848; 585/844
[58] Field of Search ............... 585/848, 844, 845; 260/438.1

[56] References Cited

U.S. PATENT DOCUMENTS

| 2,386,357 | 10/1945 | Schulze et al. | 585/845 X |
| 2,494,546 | 1/1950 | Fasce | 585/846 |
| 2,497,159 | 2/1950 | Fasce | 585/848 |
| 3,080,437 | 5/1963 | Sandberg et al. | 585/846 |
| 3,130,243 | 4/1964 | Dunn et al. | 585/844 |
| 3,517,080 | 6/1970 | Beckham et al. | 585/845 |
| 3,634,530 | 1/1972 | Bills | 585/848 |
| 3,763,200 | 10/1973 | Dines | 585/845 |
| 4,025,574 | 5/1977 | Tabler et al. | 585/848 |
| 4,129,605 | 12/1978 | Tabler et al. | 585/848 |
| 4,141,925 | 2/1979 | Pavlov et al. | 585/848 |

Primary Examiner—Helen M. S. Sneed

[57] ABSTRACT

A process and apparatus for separating monoolefins from other monoolefins comprising contacting a mixture of different monoolefins with a complexing agent selected from the group consisting of copper (I) salts of sulfonic acids and copper (I) salts of dialkyl phosphates and a suitable hydrocarbon solvent for the complexing agent under such conditions that the monoolefins form different strength complexes with the complexing agent. The different strength of the complexes provides a mechanism by which even closely boiling monoolefin isomers may be separated.

11 Claims, 1 Drawing Figure

SEPARATION OF MONOOLEFINS FROM OTHER MONOOLEFINS

This invention relates to process and apparatus for separating monoolefins from other monoolefins. In one aspect this invention relates to process and apparatus for separating monoolefin isomers which have closely similar boiling points.

In chemical processing, the separation of similar compounds has always presented difficulties. Monoolefins which have closely similar boiling points may be extremely difficult to separate and this is particularly true of monoolefin isomers which have closely similar boiling points. It is thus an object of this invention to provide process and apparatus for separating monoolefins from other monoolefins. It is another object of this invention to provide process and apparatus for separating monoolefin isomers which have closely similar boiling points.

In accordance with the present invention, a process and apparatus is provided for the separation of a monoolefin from admixture with another monoolefin by contacting a mixture of different monoolefins with a complexing agent selected from cuprous salts of sulfonic acids or dialkyl phosphates. The complexing agent is dissolved in a suitable hydrocarbon solvent for the complexing agent to form a complexing reagent. The mixture of monoolefins is contacted with the complexing reagent under such conditions that the monoolefins form different strength complexes with the complexing agent. The different strengths of the complexes provides a mechanism by which monoolefins which have closely similar boiling points may be separated.

The use of a suitable hydrocarbon solvent for the complexing agent is a critical feature of the present invention. Water is a common solvent for cuprous salts. However, aqueous solutions of cuprous salts lack stability and are generally unsuitable for forming the complexing reagent. Further, the use of a suitable hydrocarbon solvent for the complexing agent is extremely important from the standpoint of reaction time in forming the monoolefin complexes. The monoolefins form a single phase with the hydrocarbon solvent and this greatly enhances the reaction time for the formation of the monoolefin complexes. In contrast, if water is used as a solvent, the monoolefins are immiscible in the water and the complexing agent reacts very slowly with the monoolefins.

Other objects and advantages of the invention will be apparent from the foregoing brief description of the invention and the claims as well as from the detailed description of the invention and the description of the drawing in which:

FIG. 1 is a diagrammatic illustration of a separation process in accordance with one embodiment of the present invention.

The invention is described in terms of separating cis-butene-2 from trans-butene-2. However, the invention is applicable to the separation of any suitable monoolefins and especially those monoolefins which have close boiling points.

The invention is described in terms of a particular apparatus configuration. However, the invention is applicable to any apparatus which provides contact of the mixture of monoolefins with the complexing reagent with a subsequent separation and recovery of the individual monoolefins.

Referring now to the drawing, a feed stream comprising a mixture of cis-butene-2 and trans-butene-2 is provided through conduit means 11 to the separator 12. The complexing reagent which comprises the copper (I) salt complexing agent and a suitable hydrocarbon solvent for the complexing agent is provided through conduit means 15 to the separator 12. The trans-butene-2 is removed as an overhead stream from the separator 12 through conduit means 14. The cis-butene-2, which is more strongly complexed with the complexing agent than the trans-butene-2, is removed together with the hydrocarbon solvent from a lower portion of the separator 12 through conduit means 17 and is provided as a feed stream to the stripping column 18. Heat is utilized to strip the cis-butene-2 from the complexing agent. The thus stripped cis-butene-2 together with at least a portion of the hydrocarbon solvent is removed as an overhead stream from the stripper 18 through conduit means 21 and is provided to the heat exchanger 22. The heat exchanger 22 is provided with a cooling fluid through conduit means 23. The at least partially condensed stream flowing through conduit means 21 is provided from the heat exchanger 22 to the overhead accumulator 24 through conduit means 26. The cis-butene-2 will remain in gaseous form and is removed from the overhead accumulator 24 through conduit means 28. The solvent will generally be in a liquid form and will be returned as a reflux to the stripper 18 through conduit means 31. The complexing reagent will be removed from a lower portion of the stripping column 18 through conduit means 32. At least a portion of the thus removed complexing reagent will be provided through the combination of conduit means 32 and 34 to the heat exchanger 35. The heat exchanger 35 is provided with a heating fluid through conduit means 36. The thus heated complexing reagent flowing through conduit means 34 is provided from the heat exchanger 35 to the stripping column 18 through conduit means 39. The heat supplied by the complexing reagent flowing through conduit means 39 is utilized to strip the cis-butene-2 from the complexing agent.

The portion of the complexing reagent flowing through conduit means 32 which is not provided to the heat exchanger 35 is provided to the heat exchanger 41 through conduit means 42. The heat exchanger 41 is provided with a cooling fluid through conduit means 43. The thus cooled complexing reagent is provided from the heat exchanger 41 through conduit means 15 to the separator 12. The temperature in the separator 12 is generally controlled by manipulating the degree of cooling of the complexing reagent flowing through the heat exchanger 41.

At least a portion of the cis-butene-2 flowing through conduit means 28 will be removed as a product stream through conduit means 45. The remaining portion of the cis-butene-2 stream will be provided through the combination of conduit means 28 and 46 to the separator 12.

As the feed stream enters the separator 12, the cis-butene-2 and the trans-butene-2 are contacted with the complexing reagent. Both the cis-butene-2 and trans-butene-2 will be complexed with the complexing agent and will flow in liquid form towards the bottom of the separator 12. As has been previously stated, the cis-butene-2 will be more strongly complexed than the trans-butene-2. As the complexed trans-butene-2 flows towards the bottom of the separator 12, the complex is contacted with the cis-butene-2 that is recycled through conduit means 46. A ligand exchange occurs with the cis-butene-2 replacing the trans-butene-2. This results in the trans-butene-2 flowing in a gaseous form towards the upper portion of the separator 12. At the same time, the uncomplexed complexing reagent flowing through conduit means 15 will strip cis-butene-2 preferentially from the vapor phase which exists in the upper portion of the separator 12. These two actions result in a very high cis/trans ratio in the complexed olefin at the bottom of the separator 12 and a very high trans/cis ratio in the olefin vapor phase at the top of the separator 12. An effective separation of the cis-butene-2 from the trans-butene-2 has been accomplished even though the boiling points of the cis-butene-2 and trans-butene-2 are very similar.

Any suitable reaction conditions can be utilized in the process of the present invention. In general, the temperature in the separator 12 will generally be in the range of about 50° F. to about 150° F. while the pressure in the separator 12 will generally be in the range of about 1 atmosphere to about 20 psig. Preferably, the temperature in the separator 12 is maintained at least 50° F. below the boiling point of the solvent. The temperature in the stripper 18 is maintained at about the boiling point of the solvent while the pressure will generally be in the range of about 1 atmosphere to about 20 psig.

Any monoolefin can be separated from another monoolefin in accordance with the present invention so long as the two monoolefins form complexes of different strengths with the complexing agent. The process of this invention is particularly applicable to separating isomers of monoolefins which have close boiling points. In particular, isomers of butene or isomers of pentene may be separated in accordance with the process of the present invention. It is more difficult to separate isomers of hexene or heavier olefins because the large number of possible isomers reduces the probability of being able to isolate a single isomer from a large number of similar isomers. The invention is particularly applicable for accomplishing the very difficult separations of cis-butene-2 from trans-butene-2, cis-pentene-2 from trans-pentene-2, and butene-1 from isobutene.

The copper (I) salt complexing agent employed in the present invention is selected from the group consisting of:

a. the copper (I) salt of an alkane sulfonic acid having from 4 to 20 carbon atoms per molecule;
b. the copper (I) salt of an aromatic sulfonic acid including alkylaromatic, hydroxyaromatic and haloaromatic sulfonic acids having from 6 to 22 carbon atoms per molecule;
c. the copper (I) salt of a petroleum sulfonic acid; and
d. the copper (I) salt of a dialkyl phosphate having from 1 to 12 carbon atoms per alkyl member.

The presently preferred copper(I) salt is copper(I) dodecylbenzene sulfonate.

The alkane sulfonic acids useful in the practice of this invention can be straight chain or branched. Examples of suitable alkane sulfonic acids include n-butanesulfonic acid, 2-ethyl-1-hexanesulfonic acid, 2-methylnonanesulfonic acid, dodecanesulfonic acid, 2-ethyl-5-n-octyldecanesulfonic acid, n-eicosanesulfonic acid, and the like. A presently preferred alkane sulfonic acid is 2-ethyl-1-hexanesulfonic acid.

The aromatic sulfonic acids useful in the practice of this invention include benzenesulfonic acid, alkylbenzenesulfonic acids wherein the alkyl member contains from 1 to 16 carbon atoms, such as p-toluenesulfonic acid, p-dodecylbenzenesulfonic acid, p-hexadecylbenzenesulfonic acid, and the like, naphthalenesulfonic acid, phenolsulfonic acid, naphtholsulfonic acids, and halobenzenesulfonic acids, such as p-chlorobenzenesulfonic acid, p-bromobenzenesulfonic acid, and the like. A presently preferred aromatic sulfonic acid is p-dodecylbenzenesulfonic acid. Commercially available mixtures of o-, m-, and p-dodecylbenzenesulfonic acid can be employed. Preferably, the mixture employed is predominantly, i.e., 85–90 mole percent, the para isomer.

The petroleum sulfonic acids useful in the practice of this invention can be prepared from a deasphalted, solvent-refined petroleum fraction having a viscosity of about 140 to about 720 SUS at 210° F. (99° C.). A presently preferred sulfonation stock is a propane-fractionated, solvent-extracted, dewaxed Mid-Continent oil of about 200 to 230 SUS at 210° F. (99° C.) and having a viscosity index of about 90 to 100, or higher. A Mid-Continent oil is more precisely defined as a mixed base or intermediate base oil in "The Science of Petroleum", volume 1, page 7, Oxford University Press, London, New York and Toronto, 1938. Such oil is, for example, sulfonated with a 10 percent $SO_3$—90 percent $SO_2$ mixture in a continuous operation substantially as described in U.S. Pat. No. 3,135,693 to Whitney et al, using an $SO_3$ to oil weight ratio of about 0.08 and a reaction temperature of about 115° F. (46° C.). The total reaction time is about 5 minutes, including the mixing and soaking periods. The system is maintained in the liquid phase at a pressure of 100–120 psig (793–931 kPa). Effluent from the reaction unit is subjected to a two-stage flash for $SO_3$-$SO_2$ removal.

The dialkyl phosphates useful in the practice of this invention include dimethyl phosphate, diethyl phosphate, di-n-butyl phosphate, di-2-ethylhexyl phosphate, di-n-dodecyl phosphate, and the like.

The cuprous salts complexing agent of the present invention is generally prepared by refluxing a solution of the sulfonic acid or dialkyl phosphate in an inert diluent, as hereinafter described, together with cuprous oxide, with provision for removing the water of reaction, such as Dean-Stark trap. The preparation is carried out in an oxygen-free inert atmosphere such as under nitrogen. The molar ratio of acid or dialkyl phosphate to copper is preferably about 1 to 1. The preparation is carried out for a time sufficient to produce substantially complete reaction. The copper (I) salts can, if desired, be separated from the diluent by removing the diluent as by vacuum distillation.

The cuprous salts complexing agent may be utilized in any suitable hydrocarbon solvent. The cuprous salts are normally used at about a 0.5 to 2 molar solution in a hydrocarbon solvent such as paraffinic and aromatic hydrocarbon solvents having from about 5 to about 15 carbon atoms to produce a solution or slurry of the complexing reagent. The choice of solvent is related to the boiling point of the feedstock. The boiling point of the solvent is preferably at least 50°–60° F. (28°–33° C.) higher than the boiling point of the feedstock. Examples of suitable aromatic solvents include benzene, the alkyl derivatives of benzene, as for example, toluene, the xylenes, isopropyl benzene, 1,3,5-trimethylbenzene, 1,2,4,5-tetramethylbenzene, hexamethylbenzene, polynuclear aromatic hydrocarbons such as naphthalene, anthracene, and the like. Examples of suitable paraffinic solvents include n-hexane, n-octane, n-decane and the like. The solvent used in forming the cuprous salt complexing reagent for separation of normally liquid olefins is dictated by the boiling point of the olefin or the feedstock containing it. The aromatic solvents are more preferred than the paraffinic solvents because a solution of the copper(I) salt and an aromatic solvent is more stable than a solution of the copper (I) salt and a paraffinic solvent.

It is desirable to have as much of the copper (I) salt in the complexing reagent as possible. The higher the salt/solvent ratio, the greater will be the complexing capacity of the system, and the greater the amount of unsaturated hydrocarbon that can be complexed. Salt/solvent molarities of at least 0.5 mole of salt per liter of solvent have given highly satisfactory results. However, at a molarity of about 2 or more, the solution viscosity can increase enough to cause pumping difficulties, and such viscous solutions are preferably avoided.

The advantages of employing the cuprous salts of this invention over other cuprous compounds such as cuprous halides are numerous. These include low corrosivity of process equipment, particularly those fabricated from stainless steel, and water tolerance. In addition, the cuprous salts of this invention, depending upon the nature of the hydrocarbon portion of the molecule, are soluble in both aromatic and paraffinic hydrocarbon solvents whereas the cuprous halides are soluble in aromatic hydrocarbons by virtue of forming weak pi-complexes with the aromatic, hence it is not expected to be soluble in aliphatic hydrocarbons. The presently preferred cuprous salt of this invention, i.e., copper(I) dodecylbenzene sulfonate, also forms a weak pi-complex, but this is apparently not the only mechanism of solubility because the cuprous sulfonate is also soluble in aliphatic hydrocarbons.

The strength of a complex between an olefin and the complexing agent is proportional to the equilibrium constant K for the reaction $$RSO_3Cu.AR + OL \rightleftharpoons RSO_3Cu.OL + AR \quad (1)$$

where
$RSO_3Cu.AR$ = concentration of the chemical complex formed by the complexing agent and the solvent;
$RSO_3Cu.OL$ = concentration of the chemical complex formed by the complexing agent and the monoolefin;
$OL$ = concentration of the uncomplexed olefin; and
$AR$ = concentration of the uncomplexed solvent.
The equilibrium constant K for the reaction set forth in Equation (1) is defined as $$K = ([RSO_3Cu.OL][AR])/([RSO_3Cu.Ar][OL]) \quad (2)$$

Table I sets forth the equilibrium constant K for the reaction of various olefins with a copper (I) dodecylbenzene sulfonate in p-xylene complexing reagent.

TABLE I

| Olefin | K | Temp., °C. |
|---|---|---|
| Ethylene | 1.31 | 27.5 |
| Propylene | 1.72 | 24 |
| Butene-1 | 6.60 | 23 |
| Isobutene | 4.74 | 23 |
| cis-Butene-2 | 7.53 | 24 |
| trans-Butene-2 | 2.69 | 21 |

It can be seen from Table I that the process of the present invention would be very effective in separating cis-butene-2 from trans-butene-2. The data presented in Table I also indicates that the invention would be effective for separating butene-1 from isobutene.

The following examples are presented in further illustration of the invention.

EXAMPLE I

A copper (I) sulfonate complexing reagent was prepared by mixing 649 grams (2.0 mols) of dodecylbenzene sulfonic acid with 143.1 grams (1.0 mol) of cuprous oxide in 3 liters of boiling xylene under a blanket of dry nitrogen. Water formed by the reaction of the acid and oxide was collected and removed. The resulting complexing reagent was copper (I) dodecylbenzene sulfonate in xylene.

The thus prepared complexing reagent was introduced into an upper portion of a 20-tray, one-inch diameter Oldershaw column. An approximately equal molar mixture of butene-1 and isobutene was introduced into a lower portion of the Oldershaw column. An overhead stream from the Oldershaw column was collected in a trap maintained at the temperature of dry ice. A bottom stream from the Oldershaw column was collected in a kettle held at the temperature indicated in Table II. The butene-1 and isobutene in the bottoms product stream were stripped from the mixture in the kettle by heating the contents of the kettle to about 143° C. An analysis of the various products and process conditions in a plurality of runs involving the separation of butene-1 from isobutene are set forth in Table II.

TABLE II

| Run | 1 | 2 | 3 | 4 | 5 | 6 | 7 | 8 |
|---|---|---|---|---|---|---|---|---|
| Run duration, min. | 60 | 60 | 45 | 30 | 30 | 30 | 30 | 30 |
| Solvent rate, mL/min. | 11 | 29 | 50 | 50 | 50 | 78 | 78 | 78 |
| Cu(I) molarity | 0.779 | 0.779 | 0.779 | 0.791 | 0.791 | 0.791 | 0.791 | 0.791 |
| Butene feed rate, g/min. | 2.42 | 2.54 | 6.66 | 6.66 | 66.6 | 6.92 | 6.92 | 6.92 |
| Total butene feed, g | 144.9 | 152.2 | 299.7 | 199.8 | 199.8 | 207.6 | 207.6 | 207.6 |
| Wt. % isobutene | 49.5 | 49.5 | 49.5 | 49.5 | 49.5 | 49.5 | 51.6 | 51.6 |
| Wt. % butene-1 | 50.5 | 50.5 | 50.5 | 50.5 | 50.5 | 50.5 | 48.4 | 48.4 |
| Overhead products, g | 73.9 | 45.3 | 73.7 | 84.0 | 109.8 | 33.4 | 79.0 | 94.6 |
| Wt. % isobutene | 64.4 | 76.7 | 72.2 | 66.2 | 62.1 | 89.8 | 78.1 | 72.8 |
| Wt. % butene-1 | 35.6 | 23.3 | 27.8 | 33.8 | 37.8 | 10.2 | 21.9 | 27.2 |
| Stripper product, g | 43.4 | 87.0 | 130.2 | 113.9 | 98.2 | 178.3 | 131.9 | 115.3 |
| Wt. % isobutene | 27.6 | 34.7 | 34.9 | 37.7 | 35.6 | 41.6 | 35.7 | 34.8 |
| Wt. % butene-1 | 72.4 | 65.3 | 65.1 | 62.3 | 64.4 | 58.4 | 64.3 | 65.2 |
| Kettle temp., °F. | 95 | 175 | 100 | 100 | 210 | 100 | 200 | 220 |

The data presented in Table I indicate that the butene-1 is more strongly complexed than the isobutene. Thus, the isobutene concentration should be greatest in the overhead product and the butene-1 concentration should be greatest in the bottoms product flowing from the Oldershaw column. The data set forth in Table II illustrates that the isobutene/butene-1 ratio has increased substantially in the overhead product when compared with the feed while the butene-1/isobutene ratio has increased substantially in the bottoms product when compared to the feed. This indicates that the separation of butene-1 and isobutene may be accomplished in accordance with the process of the present invention.

EXAMPLE II 200 ml of a 0.777 molar solution of copper (I) dodecylbenzene sulfonate in m-xylene was prepared as described in Example I. The copper (I) dodecylbenzene sulfonate in n-xylene together with 10 grams of pentene-2 (75.52% cis, 24.48% trans) were placed in a distilling flask. The mixture in the distilling flask was distilled through a fractionating column. The resulting distillate was sequentially collected in five approximately 10 ml fractions. The boiling point of these five collected fractions and their composition as determined by gas-liquid chromatography are shown in Table III.

TABLE III

| Fraction | B.Pt., °C. | Wt., g | Total Sample | | Pentene-2 | |
| | | | Pentene-2 | Xylene | cis | trans |
| --- | --- | --- | --- | --- | --- | --- |
| 1 | 128 | 7.5 | 65.1 | 34.9 | 69.3 | 30.7 |
| 2 | 134 | 9.6 | 31.4 | 68.6 | 78.6 | 21.4 |
| 3 | 136 | 10.2 | 17.7 | 82.3 | 85.4 | 14.6 |
| 4 | 137 | 9.1 | 10.3 | 89.7 | 90.1 | 9.9 |
| 5 | 137.5 | 8.8 | 7.0 | 93.0 | 91.5 | 8.5 |

The data set forth in Table III illustrate that the relative concentrations of the cis-pentene-2 and trans-penetne-2 change markedly during the distillation. This again indicates that the process of the present invention is applicable to separating isomers of monoolefins and specifically for separating cis and trans isomers of pentene-2. This separation cannot be achieved by simple fractionation since the difference between the normal boiling points of cis and trans isomers of pentene-2 is about 1.06° F.

Reasonable variations and modifications are possible within the scope of the disclosure and the appended claims to the invention.

That which is claimed is:

1. A process for at least partially separating a first monoolefin from admixture with a second monoolefin, wherein said first monoolefin forms a stronger complex than said second monoolefin with a complexing agent selected from the group consisting of copper (I) salts of sulfonic acids and copper (I) salts of dialkyl phosphates, said process comprising the steps of:
    contacting the mixture of said first monoolefin and said second monoolefin with said complexing agent and a suitable hydrocarbon solvent for said complexing agent under such conditions that said first monoolefin forms a stronger complex than said second monoolefin with said complexing agent; and
    separating said first monoolefin from said second monoolefin based on the relative strengths of the first monoolefin complex and the second monoolefin complex.

2. A method in accordance with claim 1 wherein said step of separating said first monoolefin from said second monoolefin based on the relative strengths of the first monoolefin complex and the second monoolefin complex comprises:
    separating said second monoolefin from said complexing agent and from the mixture which contains the complexed first monoolefin and said suitable hydrocarbon solvent; and
    separating said first monoolefin from said complexing agent and said suitable hydrocarbon solvent.

3. A process in accordance with claim 1 wherein said complexing agent is selected from the group consisting of:
    (a) the copper(I) salt of an alkane sulfonic acid having from 4 to 20 carbon atoms per molecule;
    (b) the copper(I) salt of an aromatic sulfonic acid including alkylaromatic, hydroxyaromatic and haloaromatic sulfonic acids having from 6 to 22 carbon atoms per molecule;
    (c) the copper (I) salt of a petroleum sulfonic acid; and
    (d) the copper(I) salt of a dialkyl phosphate having from 1 to 12 carbon atoms per alkyl member.

4. A process in accordance with claim 1 wherein said complexing agent is copper(I) dodecylbenzene sulfonate.

5. A process in accordance with claim 2 wherein said second monoolefin is separated from said complexing agent and from the mixture which contains the complexed first monoolefin and said suitable hydrocarbon solvent by contacting the solution which results from the contacting of the mixture of said first monoolefin and said second monoolefin with said suitable hydrocarbon solvent and said complexing agent with an additional quantity of said first monoolefin, said additional quantity of said first monoolefin replacing said second monoolefin in the complexed second monoolefin to thereby separate said second monoolefin from said complexing agent and from the mixture which contains the complexed first monoolefin and said suitable hydrocarbon solvent.

6. A process in accordance with claim 5 wherein said first monoolefin is separated from said complexing agent and said suitable hydrocarbon solvent by subjecting the mixture which contains the complexed first monoolefin and said suitable hydrocarbon solvent to heat.

7. A process in accordance with claim 1 wherein said first monoolefin is butene-1 and said second monoolefin is isobutene.

8. A process in accordance with claim 1 wherein said first monoolefin is cis-butene-2 and said second monoolefin is trans-butene-2.

9. A process in accordance with claim 1 wherein said first monoolefin is cis-pentene-2 and said second monoolefin is trans-pentene-2.

10. A process in accordance with claim 1 wherein said suitable hydrocarbon solvent is a paraffinic or aromatic hydrocarbon solvent having from 6 to 15 carbon atoms.

11. A process in accordance with claim 10 wherein said suitable hydrocarbon solvent is a xylene.

* * * * *